(12) United States Patent
Beller

(10) Patent No.: US 7,591,264 B2
(45) Date of Patent: Sep. 22, 2009

(54) DEVICE FOR SWALLOWING POWDER GRANULAR OR GRANULATED SUBSTANCES

(75) Inventor: Klaus-Dieter Beller, Kenzinger (DE)

(73) Assignee: Braunform GmbH, Bahlingen (DE)

( * ) Notice: Subject to any disclaimer, the term of this patent is extended or adjusted under 35 U.S.C. 154(b) by 718 days.

(21) Appl. No.: 10/541,037

(22) PCT Filed: Dec. 19, 2003

(86) PCT No.: PCT/DE03/04194

§ 371 (c)(1), (2), (4) Date: Jun. 28, 2005

(87) PCT Pub. No.: WO2004/060458

PCT Pub. Date: Jul. 22, 2004

(65) Prior Publication Data

US 2006/0180148 A1    Aug. 17, 2006

(30) Foreign Application Priority Data

Jan. 3, 2003   (DE) ................. 103 00 032

(51) Int. Cl.
  *B65D 83/06*   (2006.01)
  *A61M 16/10*   (2006.01)
  *B67D 5/00*    (2006.01)
  *A01C 15/04*   (2006.01)

(52) U.S. Cl. .............. 128/203.15; 222/636; 128/203.12

(58) Field of Classification Search ........... 128/200.24, 128/203.12, 202.17, 203.15, 203.18, 203.22, 128/200.23, 200.14; 222/452, 488, 484, 222/142.6, 370, 367, 362, 636, 633; 221/256, 221/257, 263, 264, 265, 266

See application file for complete search history.

(56) References Cited

U.S. PATENT DOCUMENTS

| 1,139,831 | A | * | 5/1915 | Barrows ................. 222/438 |
| 2,613,018 | A | * | 10/1952 | Truitt ................... 222/452 |
| 4,524,769 | A | * | 6/1985 | Wetterlin ............... 128/203.15 |
| 5,186,164 | A | * | 2/1993 | Raghuprasad ........... 128/200.14 |
| 5,447,151 | A |   | 9/1995 | Bruna et al. ........... 128/203.15 |
| 5,505,196 | A | * | 4/1996 | Herold et al. .......... 128/203.15 |

(Continued)

FOREIGN PATENT DOCUMENTS

DE    43 19 514    12/1994

(Continued)

*Primary Examiner*—Justine R Yu
*Assistant Examiner*—Arundipta Shome
(74) *Attorney, Agent, or Firm*—Gudrun E. Huckett

(57) ABSTRACT

A device for taking powdered substances has a storage receptacle and a supply tube having a first end for dispensing the substances and a pivotably supported second end that has a unitary cylinder wall pivotably mounted on a stationary cylinder body having a through bore. The supply tube is pivotable back and forth between a first position of non-use and a second position of use. In the first position, the substance is air-tightly closed off in the storage receptacle. In the second position, the substance enters the supply tube. The unitary cylinder wall has a through opening. The supply tube has an inner opening. In the first position, the inner opening of the supply tube and the through opening of the unitary cylinder wall do not communicate with the through bore of the cylinder body; in the second position, they communicate with the through bore of the cylinder body.

5 Claims, 3 Drawing Sheets

U.S. PATENT DOCUMENTS

| | | | | |
|---|---|---|---|---|
| 5,769,073 A | 6/1998 | Eason et al. | ............ | 128/203.15 |
| 5,840,279 A | 11/1998 | Narodylo et al. | ............... | 424/46 |
| 6,029,661 A | 2/2000 | Whaley et al. | ......... | 128/203.15 |
| 6,041,779 A | 3/2000 | Juusela | .................. | 128/203.15 |
| 6,055,980 A * | 5/2000 | Mecikalski et al. | .... | 128/203.15 |
| 6,065,471 A * | 5/2000 | Schaeffer et al. | ....... | 128/203.15 |
| 6,071,498 A | 6/2000 | Narodylo et al. | ............... | 424/46 |
| 6,119,688 A | 9/2000 | Whaley et al. | ......... | 128/203.15 |
| 6,722,363 B1 | 4/2004 | Von Schuckmann | ... | 128/203.15 |
| 6,752,147 B1 * | 6/2004 | Goldemann et al. | .... | 128/203.15 |
| 6,845,772 B2 * | 1/2005 | Braithwaite et al. | .... | 128/203.15 |
| 7,089,934 B2 * | 8/2006 | Staniforth et al. | ...... | 128/203.15 |
| 7,207,330 B1 * | 4/2007 | Braithwaite | ............ | 128/203.15 |

FOREIGN PATENT DOCUMENTS

FR     2 701 653     8/1994

* cited by examiner

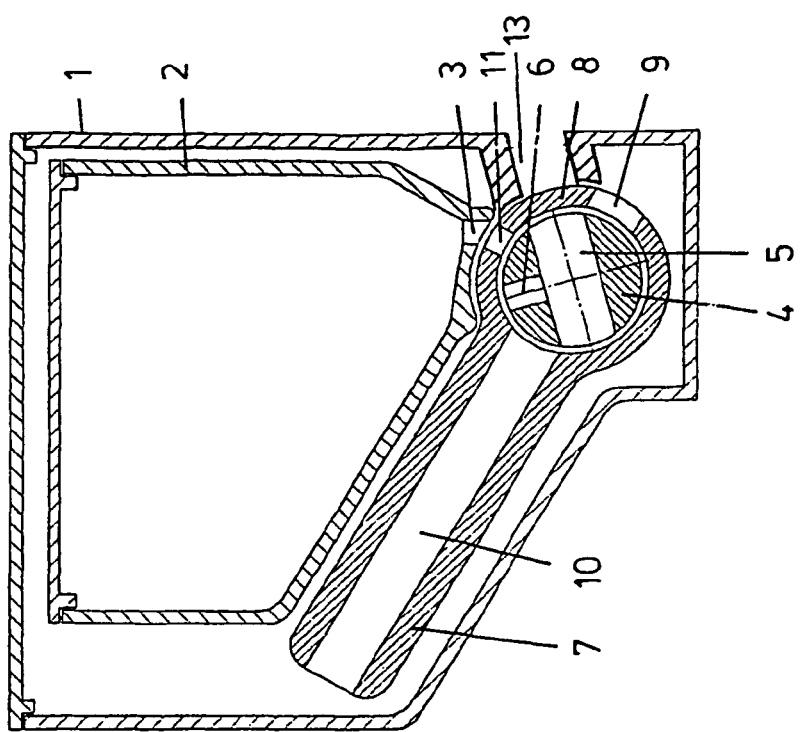
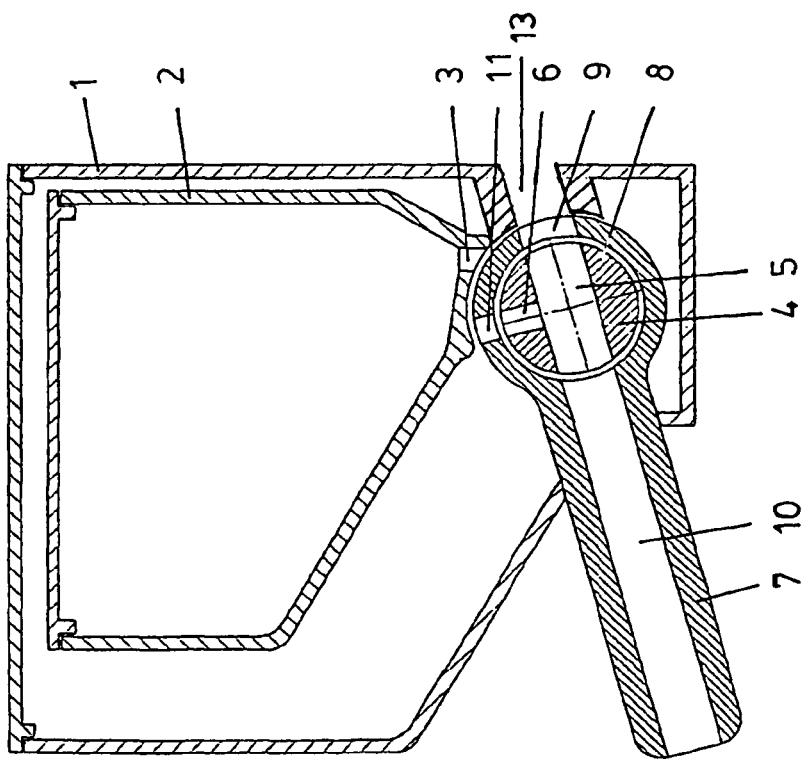

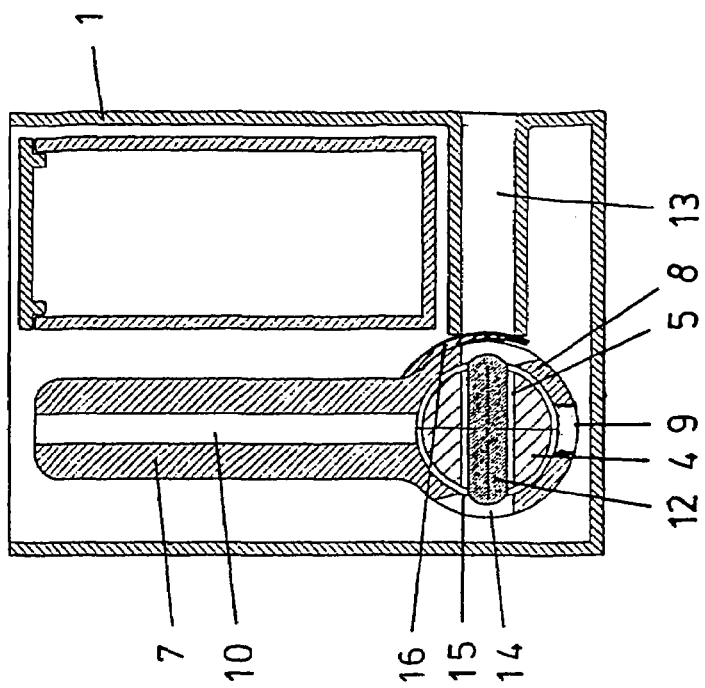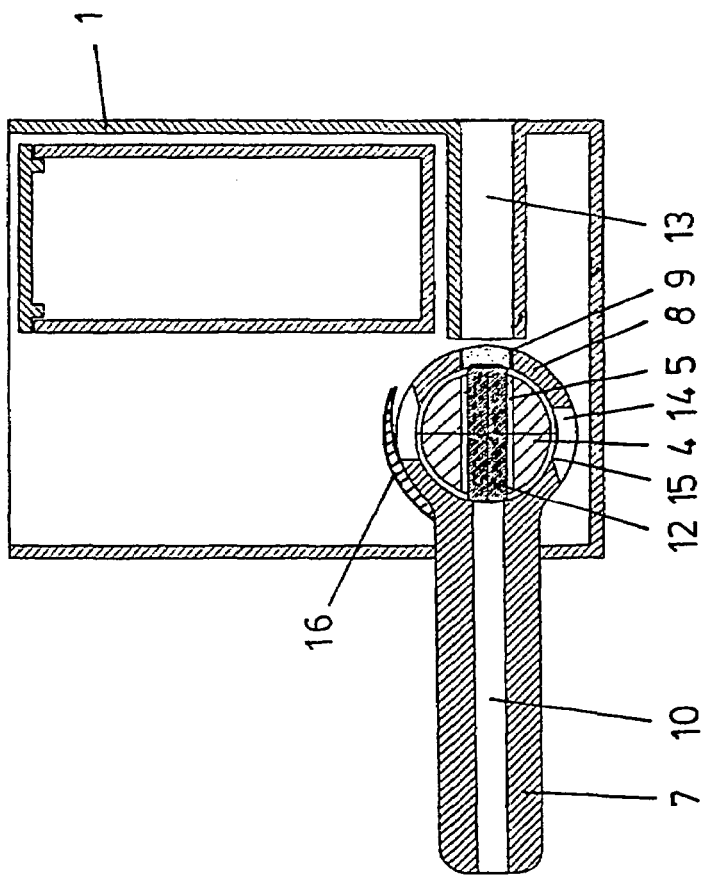

DEVICE FOR SWALLOWING POWDER GRANULAR OR GRANULATED SUBSTANCES

BACKGROUND OF THE INVENTION

The invention relates to a device for taking powdered, grainy or granular substances, wherein the device comprises a storage receptacle for the substance as well as a supply tube for supplying the substance.

One type of application of the device according to the invention for taking especially powdered substances is a so-called powder inhaler. A further type of application are devices for taking especially grainy or granular substances, for example, food supplements. The latter are characterized in that they are comprised of relatively large granules and therefore cannot be inhaled. These substances are, for example, taken orally by being supplied to the mouth. However, it is also conceivable that these grainy or granular substance can be supplied from the dosage dispenser according to the invention to drinks or other foodstuffs.

The powder inhaler according to the invention operated without propellant serves for administration by inhaling of powdered, solid medicaments or food supplements. The powder inhalers release the aerosol by means of the inhalation process wherein the energy for the dispersion is provided by inhalation. The powdered substance is contained in a storage receptacle, i.e., in a storage container, a capsule or in a blister. In this connection, the powders to be inhaled are galenic products that have been developed especially for the respective inhaler. Depending on the type of powder inhaler, the pure active ingredient is employed or the active ingredient together with a carrier (innocuous auxiliary material, usually lactose or glucose) for adhering active ingredient particles. A further possibility of providing reliably powder inhalers resides in that the micronized active ingredient is formed as soft and easily destroyable agglomerates.

In the case of currently known powder inhalers, the patient inhales a fine powder wherein the patient himself supplies the energy for generating the aerosol by means of his breathing action. This has the advantage that no coordination problems between release and inhalation are present. The active ingredient is swirled, for example, in a spirally guided airflow and reaches together with the airflow directly the bronchial tubes. However, in the case of the prior art powder inhalers, the patient when experiencing acute breathing problems is not always able to generate the required inhalation power for the powder aerosol treatment because of resistance in the air channel.

The known powder inhalers are characterized in that at any time they have an open air channel into which moisture and dirt from the surroundings can penetrate. For this reason, the known powder inhalers are provided with protective caps as well as storage devices as a protection against moisture and dirt from the surroundings. When losing or incorrectly applying such protective devices, the powder inhaler loses its full functionality. A disadvantage in regard to the known powder inhalers is that the patient not always avoids to also exhale in the opposite direction, i.e., in the exhalation direction through the inhaler. Accordingly, because of moisture within the breath, the inhaler has the tendency to cause clumping of the powder and adhering of the powder in the air channel of the inhaler. This leads also to significant dosing problems. The patient must provide the energy for generating the aerosol with his breathing action during inhalation. This energy however is limited in particular in the case of patients, and, in the case of acute breathing problems, the patient is unable to sufficiently generate the necessary energy for the required breathing power for the powder aerosol treatment in customary inhalers. Most known powder inhalers have no optimal flow course because, as a result of the constructive design defaults, flow deflection and swirling occur. This means an increased flow resistance and requires an increased energy expenditure from the patient. Finally, portions of the powder remain adhered to undercuts and in dead zones of the flow; this is detrimental with regard to the dosing precision.

The grainy or granular substances have been administered in the past in that they are removed by a spoon from the storage receptacle; subsequently, the substance is inserted with the spoon into the mouth or the substance is added to a drink or to food. This is often unhygienic because the substance is contained unprotected and freely accessible within the storage receptacle. Moreover, the required dosing precision is not always ensured.

SUMMARY OF THE INVENTION

Based on this, the invention has the object to provide a device of the aforementioned kind for taking powdered, grainy or granular substances which device is improved with regard to its function.

The technical solution is characterized in that the supply tube with its rearward end is pivotably supported by means of a unitary cylinder wall on a stationary cylinder body; the cylinder body has a through bore; the cylinder wall has a through opening; in the position of non-use of the supply tube, the inner opening of the supply tube and the through opening of the cylinder wall are not located within the area of the through opening of the cylinder body; and, in the position of use of the supply tube, the inner opening of the supply tube and the through opening of the cylinder wall are located in the area of the through bore of the cylinder body in which the substance is located.

The basic principle of the device according to the invention for taking powdered, grainy, or granular substances, in particular, of the powder inhaler according to the invention, resides in that only in the in the inhalation-ready state of the device a continuous air channel with Venturi tube-like or smooth profile is made available for guiding the airflow while in the state not ready for inhalation the air channel is completely blocked so that in the intake area no air can be sucked in and in the outlet area no powder-carrying air can be sucked in, i.e., in the supply tube. In this way, exclusively at the time of application an appropriately shaped air channel enables an optimal flow course and, while providing a perforce synchronization between deposition of the powder and inhalation, the portioned powdered medicament is entrained and dispersed sufficiently along the subsequent diffusor stretch. In the closed state, on the other hand, the intake opening as well as the outlet opening is automatically closed against moisture and dust. Even in the case of acute breathing problems, the patient can still provide the breathing power required for the powder aerosol treatment with the inhaler because straight airflow channels can be realized. The synchronously operating dosing and releasing device enables the minimization of components and closes off the entire inner system of the device in an airtight and water-tight way when not in use. The patient opens the airflow channel in the device with a single movement of the supply tube. Upon doing so, the powder is deposited and can be inhaled immediately. After inhalation, the patient closes the system again with a single movement by pivoting the supply tube. When doing so, the next dose is portioned from the storage receptacle and the system is airtightly closed. By means of the pivot system, overall a perforce correct manipulation for safe administration is ensured. A one-way valve on the intake side can provide absolute seal-tightness. Since aside from the supply tube no additional devices must be moved for readying the powder inhaler for operation, during the inhalation process the major portion of the inhalation energy remains available in fact for inhalation because of the straight configuration of the airflow channel. Because only a few mechanical parts are provided on the inhaler and the airflow is guided almost linearly, only minimal proportions of the powder remain within the device, i.e., adhere to the air channel. This increases the dosing precision. By being entrained by the airflow, the powder is uniformly distributed and de-agglomerated. The air channel preferably has the shape of a Venturi tube or Laval nozzle. In addition, during transport of the powder and entrainment by the airflow optionally larger powder particles are broken up and thus comminuted by means of helical lamellas. Mechanical resistance devices/de-agglomeration devices of any shape can be positioned within the air channel in order to vary the air channel as needed and in accordance with specifications. The air channel, depending on the requirements of the powder, can be freely varied with regard to breathing res and can have the same cross-sectional shape across the entire length. The intake istance. The configurations of the air channel can be round or oval in cross-section and outlet can be, for example, funnel-shaped. By means of the Venturi tube, an optimal flow and acceleration of the inhaled airflow including entrainment and dispersion of the powdered medicament is ensured. In particular, a perforce complete emptying is ensured. The free design of the air channel enables the adaptation of the inhaler to different inhalable medicaments. For example, dry powdered medicaments can be dispersed within the airflow in particle-defined size. The inhaler according to the invention as a hole is suitable for extended use because, due to the configuration, the entire air channel can be easily cleaned by means of a pipe cleaner and hygienic problems can be avoided. The inhaler, for full functionality and simplest shape, is comprised of a few injection-molded parts without using springs and levers. Above, the invention has been explained with the aid of a powder inhaler. The same advantages result also for grainy or granular substances which, however, are not inhaled but instead flow in a dosed portion from the device according to the invention and can be used accordingly. The difference to the powder inhaler is that no continuous airflow for inhalation is generated by the user.

A technical realization of the device according to the invention resides in that the supply tube with its rearward end is pivotably supported by means of a unitary cylinder wall on a stationary cylinder body, in that the cylinder body has a through bore and the cylinder wall has a through opening, wherein, in the position of non-use of the supply tube, the inner opening of the supply tube and the through opening of the cylinder wall are not located within the area of the through opening of the cylinder body, and, in the position of use of the supply tube, the inner opening of the supply tube and the through opening of the cylinder wall are located in the area of the through bore of the cylinder body in which the substance is located. Accordingly, at the end remote from the mouth the supply tube is rotatably supported. In the position of non-use of the device, all openings are closed while in the position of use they are open. In particular, in the case of a powder inhaler the airflow can be configured to be linear. This reduces the risk of turbulences as well as flow resistance to a minimum; this is so because the adhesion and friction play an important role when manufacturing and administering powder aerosols. During administration of the powder aerosol, adhesion and friction between medicament and auxiliary means must be overcome. However, these forces between the powder particles and the powder inhaler surface occur at the same time. Therefore, the linear profile of the airflow is advantageous.

A first application of the device according to the invention proposes that in the storage receptacle the substance is contained within several dosing units and that the storage receptacle has at a bottom side an outlet opening. The through opening of the cylinder wall, in the position of non-use of the supply tube, is located underneath the outlet opening of the storage container and, in the position of use of the supply tube, is in communication with the through bore of the cylinder body. The design is based on a reservoir for the substance from which several dosage units can be dosed.

The basic idea of the powder inhaler according to another embodiment resides in that the cylinder body has a radial through bore as well as an upwardly extending continuous connecting bore extending transversely to the through bore, wherein the radial through bore during inhalation defines a continuous airflow that entrains the substance present within the through bore. The cylinder wall has an opening in the axial extension of the supply tube and the through opening of the cylinder wall, in the position of non-use of the supply tube, is located underneath the outlet opening of the storage receptacle and, in the position of use of the supply tube, is positioned above the connecting bore of the cylinder body. The cylinder wall of the supply tube has a through opening in the form of a bore whose height and diameter determines the metering volume and matches an oppositely positioned bore in the central cylinder body. In the closed state, the through opening of the cylinder wall is positioned precisely underneath the outlet opening of the storage receptacle so that dosing of the medicament is realized. In the folded-down state of the supply tube, the medicament than flows through the connecting bore in the cylinder body into the through bore and thus precisely into the air channel so that the medicament can be inhaled upon inhalation. The storage receptacle can be exchangeable for increasing economic efficiency.

A further development based thereon proposes a one-way valve in the air channel so that the patient can only inhale the powder but cannot blow it out of the inhaler.

Another embodiment does not concern a powder inhaler but a device for dosing grainy or granular substances. The cylinder body has an angled through bore with a slant that is continuous relative to the earth's horizontal and the through opening in the cylinder wall is arranged and configured such that the through opening, in the position of non-use of the supply tube, is located underneath the outlet opening of the storage receptacle while the through bore is closed by the cylinder wall, and the through opening, in the position of use of the supply tube, is located above the inlet of the through bore of the cylinder bore and the inner opening of the supply tube communicates with the outlet of the through bore. The basic idea here is that the substance flows through the outlet opening of the storage receptacle into the through opening in the cylinder which defines a dosing chamber. After pivoting of the supply tube into the position of use, the substance flows from this dosing chamber into the through bore of the cylinder body and from there into the supply tube.

A second application of the device according to the invention proposes that the storage receptacle is a capsule for a single dosage unit and the capsule is insertable into the through bore of the cylinder body, wherein the two ends of the capsule project such past the outer surface of the cylinder body that upon pivoting of the supply tube from the position of non-use into the position of use these ends are sheared off This concerns a single-dose applicator employing a capsule. In this single-dose dosing device, the capsule is positioned in the cylinder body on the axis of rotation of the supply tube. By folding down the supply tube, the ends of the capsule are cutoff by means of a cutting blade. In this way, a complete emptying of the capsule is possible. No splinters are produced. In contrast to other devices, it is not necessary to provide a protective screen that would increase the breathing resistance. An unopened capsule can be inserted only in the position of non-use into the supply tube. This holds true also for disposal of an emptied capsule. In this way, a perforce synchronization is realized in that the cuffing of the capsule and the activation are realized in the appropriate pivot position of the supply tube while in the position of non-use an air-tight and water-tight closure of the supply tube is realized.

BRIEF DESCRIPTION OF THE DRAWINGS

Three embodiments of the device according to the invention for taking powdered, grainy or granular substances will be explained in the following with the aid of the drawings. It is shown in:

FIG. 1a a first embodiment of a powder inhaler for several dosage units (so-called multi-dose) in the position of non-use;

FIG. 1b the powder inhaler of FIG. 1a in the position of use;

FIG. 2a a second embodiment of the powder inhaler for a single dosage (so-called single-dose) in the position of non-use;

FIG. 2b the powder inhaler of FIG. 2a in the position of use;

DESCRIPTION OF PREFRERRED EMBODIMENTS

Figure 3:
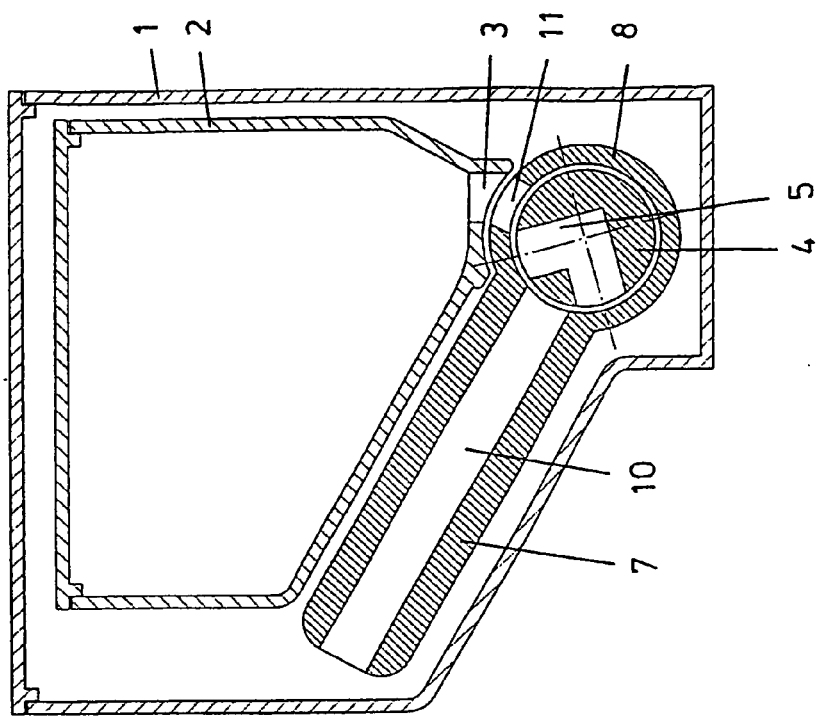
FIG. 3a a third embodiment as a device for taking grainy or granular substances for several dosage units (so-called multi-dose) in the position of non-use.
FIG. 3b the device of FIG. 3a in the position of use.
Figure 3:
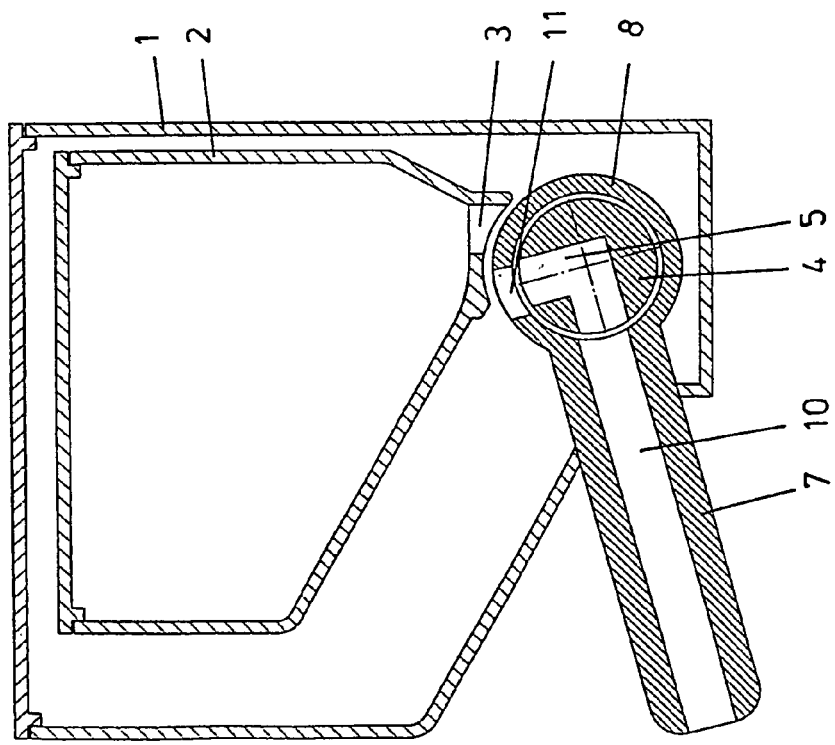

The powder inhaler of the first embodiment of FIGS. 1a and 1b has a housing 1 in which a substantially funnel-shaped storage receptacle 2 for powder is located. This storage receptacle 2 has an outlet opening 3 at the lowest point.

In the housing a cylinder body 4 is moreover fixedly arranged. It has a radial through bore 5. A connecting bore 6 that is also continuous branches off transversely from the through bore 5 in the upward direction.

On the cylinder body 4, a supply tube 7 in the form of an inhalation pipe is rotatably supported. For this purpose, the rearward end of the supply tube 7 has a cylinder wall 8 with which the pivoting support action on the cylinder body 4 is realized. This cylinder wall 8 has an opening 9 which is positioned on the axis of the inner opening 10 of the supply tube 7. Moreover, the cylinder wall 8 has a through opening 11.

Finally, the housing 1 has an inwardly projecting air inlet 13.

The device functions as follows:

In the position of non-use (FIG. 1a), the through opening 11 of the cylinder wall 8 is positioned underneath the outlet opening 3 of the storage container 2. The powder flows into the through opening 11 which thus defines a dosage unit. In this position, the through bore 5 as well as the connecting bore 6 of the cylinder body 4 are seal-tightly closed by the cylinder wall 8.

For transferring the powder inhaler into the position of use (FIG. 1b), the supply tube 7 is pivoted downwardly. In this way, the through opening 11 (containing the dosage unit of powder) is moved into a position above the connecting bore 6 in the cylinder body 4 so that the powder flows through the connecting bore 6 into the through bore 5. Accordingly, the inner opening 10 of the supply tube 7, the through bore 5 of the cylinder body 4, the opening 9 of the cylinder wall 8 of the supply tube 7 as well as the air inlet 13 of the housing 1 define an interconnected continuous and sealed through channel. When the user inhales, the powder is entrained and is inhaled by the patient. The inhalation tube 7 can be in principle designed as a mouth tube or nose tube.

After inhalation, the supply tube 7 is moved upwardly again (FIG. 1a) so that a new dosage of powder flows from the storage container 2 through the outlet opening 3 into the through opening 11 in the cylinder wall 8.

The second embodiment in FIG. 2a and FIG. 2b is based on a storage receptacle in the form of a capsule 12 for a single dose. With regard to the basic principle, this embodiment variant is identical to that of the powder inhaler of FIGS. 1a and 1b.

A cylinder body 4 having a through bore 5 is provided (however, without a connecting bore 6). A cylinder wall 8 of a supply tube 7 is pivotably supported on the cylinder body 4. This cylinder wall 8 has an opening 9 on the axis of the inner opening 10 of the supply tube 7. Moreover, the cylinder wall 8 has two passages 14 with a cutting edge 15, respectively. The upper passage 14 in FIG. 2b has additionally a sealing nose 16.

The function is as follows:

In the position of non-use of the powder inhaler (FIG. 2a) a capsule 12 is inserted into the through bore 5 of the cylinder body 4. The inner opening 10 of the supply tube 7 as well as the opening 9 of the cylinder wall 8 are seal-tightly closed by the cylinder body 4. Moreover, the air inlet 13 of the housing 1 is tightly closed by the sealing nose.

For transferring the powder inhaler into the position of use, the supply tube 7 is folded downwardly (FIG. 2b). When doing so, the two cutting edges 15 of the cylinder wall 8 cut off the ends of the capsule 12. Accordingly, the powder in the interior of the capsule 12 is within the airflow during the inhalation process. The sealed air channel is defined by the inner opening 10 of the supply tube 7, the through bore 5 in the cylinder 4, the opening 9 in the cylinder wall 8 as well as the air inlet 13 of the housing 1.

After completion of inhalation, the supply tube 7 is again pivoted upwardly so that the empty capsule 12 can be removed.

The third embodiment in FIGS. 3a and 3b serves for the dosed dispensing of grainy or granular substances contained within the storage receptacle 2. The difference to the powder inhaler of FIGS. 1a and 1b resides in that the cylinder wall 8 does not have the opening 9 and that the through bore 5 in the cylinder body 4 is of an angular configuration wherein this through bore 5 from the upper inlet to the lower outlet has a continuous slant relative to the earth's horizontal.

The function is as follows:

In the storage receptacle 2, as mentioned already, a grainy or granular flowable substance is contained. In the position of non-use of the device (FIG. 3a) the supply tube 7 is folded upwardly so that the through opening 11 of the cylinder wall 8 is moved into a position underneath the outlet opening 3. The through bore 5 in the cylinder body 4 is completely closed by the cylinder wall 8. In the through opening 11 of the cylinder wall 8 the grainy or granular substance is collected.

After folding down the supply tube 7 into the position of use (FIG. 3b), the through Opening 11 of the cylinder wall 8 is located in a position above the inlet of the angled through opening 5. The substance contained within the through opening 11 of the cylinder wall 8 flows from above into the through bore 5. As a result of its free flowing properties, the substance finally reach the inner opening 10 of the supply tube 7 from where the substance can be taken either orally or can be added to a drink or food or can be directly administered otherwise.

LIST OF THE REFERENCE NUMERALS 1 housing
2 storage receptacle
3 outlet opening
4 cylinder body
5 through bore
6 connecting bore
7 supply tube
8 cylinder wall
9 opening
10 inner opening
11 through opening
12 capsule
13 air inlet
14 passage
15 cutting edge
16 sealing nose

What is claimed is:

1. A device for taking powdered, grainy or granular substances, the device comprising:
   a storage receptacle for a substance;
   a supply tube having an inner opening, wherein the supply tube has a first end for dispensing the substance and a pivotably supported second end;
   a stationary cylinder body having a through bore;
   wherein the second end of the supply tube comprises a unitary cylinder wall that is pivotably mounted on the stationary cylinder body and has a through opening, wherein the supply tube is pivotable back and forth between a first position of non-use and a second position of use;
   wherein in the first position the substance is air-tightly closed off in the storage receptacle and in the second position the substance enters the supply tube;
   wherein in the first position the inner opening of the supply tube and the through opening of the unitary cylinder wall do not communicate with the through bore of the cylinder body;
   wherein in the second position the inner opening of the supply tube and the through opening of the unitary cylinder wall communicate with the through bore of the cylinder and wherein in the second position a dosage unit of the substance is present in the through bore of the cylinder body and is conveyed from the through bore into the supply tube by an air stream or flows out;
   wherein the supply tube has an inner opening;
   wherein the storage receptacle contains several dosage units of the substance, wherein the storage receptacle has a bottom side provided with an outlet opening, and wherein the through opening of the unitary cylinder wall, in the first position of the supply tube, is located underneath the outlet opening of the storage receptacle and receives a dosage unit and, in the second position, communicates with the through bore of the cylinder body so that the dosage unit drops into the through bore.

2. The device according to claim 1, wherein the through bore of the cylinder body extends radially and wherein the cylinder body further comprises an upwardly extending continuous connecting bore connected transversely to the radially extending through bore, wherein the radially extending through bore during inhalation defines a continuous airflow that entrains the substance present within the radially extending through bore, wherein the cylinder wall has a remote opening at the second end remote from the first end and provided on an axial extension of the supply tube, wherein the through opening of the cylinder wall, in the first position of the supply tube, is located underneath the outlet opening of the storage receptacle and, in the second position of the supply tube, is positioned above the connecting bore of the cylinder body.

3. The device according to claim 2, having an air channel defining the airflow, wherein the air channel has a one-way valve.

4. The device according to claim 1, wherein the through bore of the cylinder body is an angled through bore and has a slant that is continuous relative to the horizontal, wherein the through opening in the cylinder wall is arranged such that the through opening, in the first position of the supply tube, is located underneath the outlet opening of the storage receptacle while the angled through bore is closed by the cylinder wall, wherein the through opening, in the second position of the supply tube, is located above an inlet of the through bore of the cylinder bore and the inner opening of the supply tube communicates with an outlet of the angled through bore.

5. A device for taking powdered, grainy or granular substances, the device comprising:
   a storage receptacle for a substance;
   a supply tube having an inner opening, wherein the supply tube has a first end for dispensing the substance and a pivotably supported second end;
   a stationary cylinder body having a through bore;
   wherein the second end of the supply tube comprises a unitary cylinder wall that is pivotably mounted on the stationary cylinder body and has a through opening, wherein the supply tube is pivotable back and forth between a first position of non-use and a second position of use;
   wherein in the first position the substance is air-tightly closed off in the storage receptacle and in the second position the substance enters the supply tube;
   wherein in the first position the inner opening of the supply tube and the through opening of the unitary cylinder wall do not communicate with the through bore of the cylinder body;
   wherein in the second position the inner opening of the supply tube and the through opening of the unitary cylinder wall communicate with the through bore of the cylinder and wherein in the second position a dosage unit of the substance is present in the through bore of the cylinder body and is conveyed from the through bore into the supply tube by an air stream or flows out;
   wherein the storage receptacle is a capsule for a single dosage unit of the substance, wherein the capsule is insertable into the through bore of the cylinder body, and opposed ends of the capsule project such past an outer surface of the cylinder body that upon pivoting of the supply tube from the first position into the second position the opposed ends of the capsule are sheared off.

* * * * *